(12) United States Patent
Chuter et al.

(10) Patent No.: US 10,695,171 B2
(45) Date of Patent: Jun. 30, 2020

(54) STENT STRUCTURES FOR USE WITH VALVE REPLACEMENTS

(71) Applicant: COOK MEDICAL TECHNOLOGIES LLC, Bloomington, IN (US)

(72) Inventors: Timothy A. Chuter, San Francisco, CA (US); Blayne A. Roeder, Bloomington, IN (US); Sharath Gopalakrishnamurthy, Malleshwaram (IN); Alan R. Leewood, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 183 days.

(21) Appl. No.: 15/841,744

(22) Filed: Dec. 14, 2017

(65) Prior Publication Data

US 2018/0104054 A1 Apr. 19, 2018

Related U.S. Application Data

(63) Continuation of application No. 13/286,407, filed on Nov. 1, 2011.
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2220/0016* (2013.01);
(Continued)

(58) Field of Classification Search
CPC .. A61F 2/86; A61F 2/90; A61F 2/2412; A61F 2/2418
See application file for complete search history.

(56) References Cited

U.S. PATENT DOCUMENTS

| 4,222,126 A | 9/1980 | Boretos et al. |
| 4,994,077 A | 2/1991 | Dobben |

(Continued)

FOREIGN PATENT DOCUMENTS

| AU | 2003234967 A1 | 9/2003 |
| CN | 2817764 | 9/2006 |

(Continued)

OTHER PUBLICATIONS

St. Jude Medical, LLLC—European Opposition Against Application/Patent No. 11275139.1/2489331, dated Apr. 5, 2018, 39 pgs.
(Continued)

*Primary Examiner* — Brian A Dukert
(74) *Attorney, Agent, or Firm* — Brinks Gilson & Lione

(57) ABSTRACT

The present embodiments provide a medical device for implantation in a patient-comprising a stent and a valve. The stent comprises a proximal region comprising a cylindrical shape having a first outer diameter in an expanded state, and a distal region comprising a cylindrical shape having a second outer diameter in the expanded state. The second outer diameter is greater than the first outer diameter. A proximal region of the valve is at least partially positioned within the proximal region of the stent, and the distal region of the valve is at least partially positioned within one of tapered and distal regions of the stent. When implanted, the proximal region of the stent and the proximal region of the valve are aligned with a native valve, and the distal region of the valve is distally spaced-apart from the native valve.

19 Claims, 8 Drawing Sheets

Related U.S. Application Data

(60) Provisional application No. 61/410,540, filed on Nov. 5, 2010.

(52) U.S. Cl.
CPC ............... *A61F 2230/0019* (2013.01); *A61F 2230/0078* (2013.01)

(56) References Cited

U.S. PATENT DOCUMENTS

| | | | |
|---|---|---|---|
| 5,163,953 A | 11/1992 | Vince | |
| 5,332,402 A | 7/1994 | Teitelbaum | |
| 5,370,685 A | 12/1994 | Stevens | |
| 5,397,351 A | 3/1995 | Pavcnik et al. | |
| 5,755,782 A | 5/1998 | Love et al. | |
| 5,840,081 A | 11/1998 | Andersen et al. | |
| 5,855,597 A | 1/1999 | Jayaraman | |
| 5,855,600 A | 1/1999 | Alt | |
| 5,938,687 A | 8/1999 | Bouhour et al. | |
| 5,938,697 A | 8/1999 | Killion et al. | |
| 6,120,534 A | 9/2000 | Ruiz | |
| 6,168,619 B1 | 1/2001 | Dinh et al. | |
| 6,245,102 B1 | 6/2001 | Jayaraman | |
| 6,254,642 B1 | 7/2001 | Taylor | |
| 6,258,120 B1 | 7/2001 | McKenzie et al. | |
| 6,409,756 B1 | 6/2002 | Murphy | |
| 6,416,544 B2 | 7/2002 | Sugita et al. | |
| 6,440,164 B1 | 8/2002 | DiMatteo et al. | |
| 6,458,153 B1 | 10/2002 | Bailey et al. | |
| 6,482,228 B1 | 11/2002 | Norred | |
| 6,494,090 B1 | 12/2002 | Losing et al. | |
| 6,582,462 B1 | 6/2003 | Andersen et al. | |
| 6,730,118 B2 | 5/2004 | Spenser et al. | |
| 6,773,453 B2 | 8/2004 | Ravenscroft | |
| 6,773,454 B2 | 8/2004 | Wholey et al. | |
| 6,797,000 B2 | 9/2004 | Simpson et al. | |
| 6,830,584 B1 | 12/2004 | Seguin | |
| 6,911,040 B2 | 6/2005 | Johnson et al. | |
| 7,018,406 B2 | 3/2006 | Seguin et al. | |
| 7,144,421 B2 | 12/2006 | Carpenter et al. | |
| 7,192,442 B2 | 3/2007 | Solem et al. | |
| 7,201,772 B2 | 4/2007 | Schwammenthal et al. | |
| 7,220,274 B1 | 5/2007 | Quinn | |
| 7,267,686 B2 | 9/2007 | DiMatteo et al. | |
| 7,329,278 B2 | 2/2008 | Seguin et al. | |
| 7,329,279 B2 | 2/2008 | Haug et al. | |
| 7,331,991 B2 | 2/2008 | Kheradvar et al. | |
| 7,351,256 B2 | 4/2008 | Hojeibane et al. | |
| 7,377,938 B2 | 5/2008 | Sarac et al. | |
| 7,381,219 B2 | 6/2008 | Salahieh et al. | |
| 7,429,269 B2 | 9/2008 | Schwammenthal et al. | |
| 7,442,204 B2 | 10/2008 | Schwammenthal et al. | |
| 7,510,574 B2 | 3/2009 | Le et al. | |
| 7,544,206 B2 | 6/2009 | Cohn | |
| 7,556,643 B2 | 7/2009 | Casey, II et al. | |
| 7,572,286 B1 | 8/2009 | Chen et al. | |
| 7,591,848 B2 | 9/2009 | Allen | |
| 7,682,390 B2 | 3/2010 | Seguin | |
| 7,780,726 B2 | 8/2010 | Seguin | |
| 7,789,909 B2 | 9/2010 | Andersen et al. | |
| 7,799,072 B2 | 9/2010 | Greenberg | |
| 7,806,920 B2 | 10/2010 | Duran | |
| 7,857,845 B2 | 12/2010 | Stacchino et al. | |
| 7,892,281 B2 | 2/2011 | Seguin et al. | |
| 7,914,569 B2 | 3/2011 | Nguyen et al. | |
| 7,967,853 B2 | 6/2011 | Eidenschink et al. | |
| 8,016,877 B2 | 9/2011 | Seguin et al. | |
| 8,080,054 B2 | 12/2011 | Rowe | |
| 8,092,521 B2 | 1/2012 | Figulla et al. | |
| 8,167,934 B2 | 5/2012 | Styrc et al. | |
| 8,206,437 B2 | 6/2012 | Bonhoeffer et al. | |
| 8,206,438 B2 | 6/2012 | Yang et al. | |
| 8,348,996 B2 | 1/2013 | Tuval et al. | |
| 2002/0055772 A1 | 5/2002 | McGuckin et al. | |
| 2003/0040792 A1 | 2/2003 | Gabbay | |
| 2003/0074052 A1 | 4/2003 | Besselink | |
| 2003/0120333 A1 | 6/2003 | Ouriel et al. | |
| 2003/0130726 A1 | 7/2003 | Thorpe et al. | |
| 2003/0176914 A1 | 9/2003 | Rabkin et al. | |
| 2003/0199967 A1 | 10/2003 | Hartley et al. | |
| 2004/0044402 A1 | 3/2004 | Jung et al. | |
| 2004/0055606 A1 | 3/2004 | Hendricksen et al. | |
| 2004/0117003 A1 | 6/2004 | Ouriel et al. | |
| 2004/0210304 A1 | 10/2004 | Seguin et al. | |
| 2004/0236411 A1 | 11/2004 | Sarac et al. | |
| 2004/0254636 A1 | 12/2004 | Flagle et al. | |
| 2005/0075725 A1 | 4/2005 | Rowe | |
| 2005/0085900 A1 | 4/2005 | Case et al. | |
| 2005/0096736 A1 | 5/2005 | Osse et al. | |
| 2005/0102018 A1 | 5/2005 | Carpenter et al. | |
| 2005/0137682 A1 | 6/2005 | Justino | |
| 2005/0182483 A1 | 8/2005 | Osborne et al. | |
| 2005/0222674 A1 | 10/2005 | Paine | |
| 2005/0251251 A1 | 11/2005 | Cribier | |
| 2006/0149360 A1 | 7/2006 | Schwammenthal et al. | |
| 2006/0195180 A1 | 8/2006 | Kheradvar et al. | |
| 2006/0265056 A1 | 11/2006 | Nguyen et al. | |
| 2006/0276813 A1 | 12/2006 | Greenberg | |
| 2007/0118209 A1 | 5/2007 | Strecker | |
| 2007/0123972 A1 | 5/2007 | Greenberg et al. | |
| 2007/0168013 A1 | 7/2007 | Douglas | |
| 2007/0173926 A1 | 7/2007 | Bobo, Jr. et al. | |
| 2007/0213813 A1 | 9/2007 | Von Segesser et al. | |
| 2007/0239273 A1 | 10/2007 | Allen | |
| 2007/0244546 A1 | 10/2007 | Francis | |
| 2008/0039891 A1 | 2/2008 | McGuckin, Jr. et al. | |
| 2008/0082166 A1 | 4/2008 | Styrc et al. | |
| 2008/0208314 A1 | 8/2008 | Skerven | |
| 2008/0208325 A1 | 8/2008 | Helmus et al. | |
| 2008/0262593 A1 | 10/2008 | Ryan et al. | |
| 2008/0275549 A1 | 11/2008 | Rowe | |
| 2009/0099649 A1 | 4/2009 | Chobotov et al. | |
| 2009/0125098 A1 | 5/2009 | Chuter | |
| 2009/0171437 A1 | 7/2009 | Brocker et al. | |
| 2009/0198324 A1 | 8/2009 | Orlov | |
| 2010/0063577 A1 | 3/2010 | Case et al. | |
| 2010/0094411 A1 | 4/2010 | Tuval et al. | |
| 2010/0168839 A1 | 7/2010 | Braido et al. | |
| 2010/0256738 A1 | 10/2010 | Berglund | |
| 2010/0298927 A1 | 11/2010 | Greenberg | |
| 2011/0208289 A1 | 8/2011 | Shalev | |
| 2012/0053676 A1 | 3/2012 | Ku et al. | |
| 2012/0116496 A1 | 5/2012 | Chuter et al. | |
| 2012/0116498 A1 | 5/2012 | Chuter et al. | |
| 2012/0130478 A1 | 5/2012 | Shaw | |
| 2012/0283820 A1 | 11/2012 | Tseng et al. | |

FOREIGN PATENT DOCUMENTS

| | | |
|---|---|---|
| DE | 102007045188 | 6/2008 |
| EP | 1 264 582 A2 | 12/2002 |
| EP | 2 489 331 A1 | 8/2012 |
| EP | 2 489 331 B1 | 6/2017 |
| JP | 49-5434 B | 2/1974 |
| JP | 2004-500189 A | 1/2004 |
| JP | 2005-514968 A | 5/2005 |
| JP | 2008-539985 A | 11/2008 |
| JP | 2008-541865 A | 11/2008 |
| WO | WO 00/21463 A1 | 4/2000 |
| WO | WO 2000/041652 A1 | 7/2000 |
| WO | WO 01/49213 A2 | 7/2001 |
| WO | WO 03/003943 A2 | 1/2003 |
| WO | WO 2003/003943 A2 | 1/2003 |
| WO | WO 2005/011535 A2 | 2/2005 |
| WO | WO 2006/124649 A2 | 11/2006 |
| WO | WO 2006/127765 A1 | 11/2006 |
| WO | WO 2008/070797 A2 | 6/2008 |
| WO | WO 2010/008549 A1 | 1/2010 |
| WO | WO 2010/096176 A1 | 8/2010 |
| WO | WO 2010/098857 A1 | 9/2010 |
| WO | WO 2010/099032 A2 | 9/2010 |
| WO | WO 2011/025945 A2 | 3/2011 |

(56) References Cited

FOREIGN PATENT DOCUMENTS

| WO | WO 2011/106544 A1 | 9/2011 |
|---|---|---|
| WO | WO 2012/027487 A2 | 3/2012 |
| WO | WO 2012/039753 A2 | 3/2012 |

OTHER PUBLICATIONS

No. 18, Laborde, Jean-Claude et al., "The CoreValve in the Aortic Position", from the book *Transcatheter Value Repair*, by eds. Hijazi et al., copyright 2006, Taylor & Francis, United Kingdom, pp. 175-185.
Biotronik AG—European Opposition Against Application/Patent 11275139.1/ 2489331, dated Apr. 4, 2018, 48 pgs.
Dave, Rajesh M. et al, "Aortic Valvuloplasty, The State of the Art and an Introductions to Percutaneous Aortic Valve Technology.", *Cardiac Interventions Today*, Jun. 2007, pp. 51-59.
"Medtronic's Corevalve Shows Subclavian Access Success in Patients Contraindicated for Femoral Approach", Medical News Today, May 21, 2009, http://www.medicalnewstoday.com/releases/150929.php, last visited Nov. 24, 2011 1 pg.
"Medtronic's CoreValve Transcatheter Aortic Valve Replacement System Performs Well in Trial", Medgaget.com article, posted May 20, 2009, http://www.medgadget.com/archives/print/007754print.html, 3 pgs.
"Beating Heart Aortic Valve. Replacement: The Future is Here" Ashok Babu, M.D., Department of Surgery, University of Colorado, PowerPoint presentation, 33 pgs.
"Sesame Membrane Covered Stent for SVG's", Steven R. Bailey, M.D., et al., Univeristy of Texas Health Sciences Center at San Antonio, PowerPoint presentation, 33 pgs.
"Percutaneous Aortic Valve Implantation Scope of the Problem and Imaging", E Murat Tuzcu, Cleveland Clinic, 33 pgs.
"Percutaneous Implantation of the First Repositionable Aortic Valve Prosthesis in a Patent With Severe Aortic Stenosis", L. Buellesfeld, et al., Catheter Cardiovasc Interv. Apr. 1, 2008; 71(5): 579-84, 1 pg.
Cedars-Sinai Medical Center Prosthetic Heart Valve Information brochure, Cedars-Sinai Medical Center Division of Cardiology, 37 pgs.
"Percutaneous Valve Repair and Replacement", Howard C. Hermann, M.D., University of Pennsylvania Medical Center, PowerPoint presentation, 15 pgs.
"Percutaneous Approaches to Aortic Valve Replacement", Adam M. Brodsky, M.D., Applications in Imaging-Cardiac Interventions, Dec. 2004, 6 pgs.
Percutaneous Aortic Valve Implantation: Early Clinical Experience and Future Perspectives:, Danny Dvir, M.D., et al., IMAJ, vol. 11, Apr. 2009, 6 pgs.
"Percutaneous Treatment of Aortic Valve Stenosis", Inder M. Singh, M.D., et al., Cleveland Clinic Journal of Medicine, vol. 75, Num. 11, Nov. 2008, 8 pgs.
"First Human Case of Retrograde Transcatheter Implantation of an Aortic Valve Prosthesis", David Paniagua, M.D., et al., Texas Heart Institute Journal, Transcatheter Aortic Valve Prothesis, vol. 32, No. 3, 2005, 6 pgs.
"Percutaneous Transcatheter Aortic Valve Implantation: Assessing Results, Judging Outcomes, and Planning Trials: The Interventionalist Perspective", Paul T.L. Chiam, et al., J. Am. Coll. Cardiol. Intv. 2008: 1; 341-350, 12 pgs.
"Percutaneous Transcatheter Aortic Valve Implantation: Evolution of the Technology", Paul T.L. Chiam, et al., American Heart Journal, Feb. 2009, 229-42, 14 pgs.
Restriction Requirement for U.S. Appl. No. 13/286,407 dated Dec. 20, 2012, 6 pgs.
Response to Restriction Requirement for U.S. Appl. No. 13/286,407 dated Jan. 22, 2013, 7 pgs.
Office Action for U.S. Appl. No. 13/286,407 dated Feb. 15, 2013, 13 pgs.
Applicant Initiated Interview Summary for U.S. Appl. No. 13/286,407 dated Jun. 6, 2013, 3 pgs.
Response to Office Action for U.S. Appl. No. 13/286,407 dated Jul. 15, 2013, 13 pgs.
Final Office Action for U.S. Appl. No. 13/286,407 dated Sep. 24, 2013, 12 pgs.
Examination Report No. 1 in Australia Application No. 2011244968, dated Dec. 23, 2012, 3 pages.
Response to Examination Report No. 1 in Australian Application No. 2011244968, dated Oct. 17, 2013, 11 pages.
Examination Report No. 2 in Australia Application No. 2011244968, dated Oct. 22, 2013, 4 pages.
Response to Examination Report No. 2 in Australian Application No. 2011244968, dated Dec. 20, 2013, 7 pages.
Examination Report No. 3 in Australia Application No. 2011244968, dated Jan. 14, 2014, 4 pages.
Response to Examination Report No. 3 in Australian Application No. 2011244968, dated Mar. 24, 2014, 6 pages.
Notice of Acceptance in Australian Application No. 2011244968, dated Apr. 3, 2014, 3 pages.
Partial European Search Report in European Application No. 11275139.1, dated Jun. 29, 2012, 6 pages.
Extended European Search Report in European Application No. 11275139.1, dated Oct. 8, 2012, 12 pages.
Notice of Loss of Rights for EP11275139.1 dated Jun. 13, 2013, 1 pg.
Response to Notice of Loss of Rights for EP11275139.1 dated Aug. 12, 2013, 11 pgs.
Intention to Grant in European Application No. 11275139.1, dated Sep. 28, 2016, 6 pages.
Office Action, and English language translation thereof, in corresponding Japanese Application No. 2011-242377, dated Sep. 1, 2015, 4 pages.
Response to Office Action, and English language translation thereof, in corresponding Japanese Application No. 2011-242377, dated Jan. 29, 2016, 22 pages.
Office Action, and English language translation thereof, in corresponding Japanese Application No. 2011-242377, dated Jun. 8, 2016, 8 pages.
Response to Office Action, and English language translation thereof, in corresponding Japanese Application No. 2011-242377, dated Oct. 12, 2016, 6 pages.
Decision for Patent, and English language translation thereof, in corresponding Japanese Application No. 2011-242377, dated Feb. 21, 2017, 4 pages.
Patent Examination Report No. 1 for AU2011244966 dated Dec. 23, 2012, 3 pgs.
Response to Patent Examination Report No. 1 for AU2011244966 dated Jan. 22, 2014, 5 pgs.
Patent Examination Report No. 2 in Australian Application No. 2011244966, dated Jan. 28, 2014, 4 pages.
Response to Patent Examination Report No. 2 in Australian Application No. 2011244966, dated Mar. 21, 2014, 6 pages.
Notice of Acceptance in Australian Application No. 2011244966, dated Apr. 2, 2014, 2 pages.
Extended European Search Report for European Patent Application No. 11275138.3 dated Jun. 26, 2012, 6 pgs.
Response to Written Opinion for European Patent Application No. 11275138.3 filed Jan. 25, 2013, 7 pgs.
Intention to Grant in European Application No. 11275138.3, dated Oct. 5, 2016, 7 pages.
Decision to Grant a European Patent Pursuant to Aritcle 97(1) EPC in European Application No. 11275138.3, dated Apr. 6, 2017, pages.
Updated Intention to Grant in European Application No. 11275138.3, dated Mar. 15, 2017, 7 pages.
Office Action, and English language translation thereof, in Japanese Application No. 2011-242624, dated Aug. 4, 2015, 7 pages.
Office Action in U.S. Appl. No. 13/286,416, dated Oct. 24, 2013, 7 pages.
Response to Office Action in U.S. Appl. No. 13/286,416, dated Feb. 24, 2014, 17 pages.
Office Action in U.S. Appl. No. 13/286,416, dated Mar. 26, 2014, 10 pages.
Response to Office Action in U.S. Appl. No. 13/286,416, dated Jul. 28, 2014, 17 pages.

(56) References Cited

OTHER PUBLICATIONS

International Search Report and Written Opinion for PCT/US2008/012500 dated Feb. 6, 2009, 15 pgs.
Sisman, Mehtap et al., "The Comparison Between Self-Expanding and Balloon Expandable Stent Results in Left Anterior Descending Artery", International Journal of Angiology, Jan. 2001, pp. 34-40, vol. 10, No. 1, springer New York, springer Link Date Feb. 19, 2004, 2 pgs.
St. Jude Medical, LLC—European Opposition Against Application/Patent No. 11275139.1/ 2489331, dated Apr. 5, 2018, 39 pgs.
No. 16, Boudjemline, Younes et al., "Non-surgical aortic valve replacement: History, present, and future perspectives", from the book *Transcatheter Valve Repair*, by eds. Hijazi et al., copyright 2006, Taylor & Francis, United Kingdom, pp. 157-163.
No. 17, Cribier, Alain et al., "Clinical experience with the Percutaneous heart valve for treatment of degenerative aortic stenosis", from the book *Transcatheter Valve Repair*, by eds. Hijazi et al., copyright 2006, Taylor & Francis, United Kingdom, pp. 164-174.
No. 18, Laborde, Jean-Claude et al., "The CoreValve in the aortic position", from the book *Transcatheter Valve Repair*, by eds. Hijazi et al., copyright 2006, Taylor & Francis, United Kingdom, pp. 175-185.
Biotronik AG—European Opposition Against Application/Patent No. 11275139.1/ 2489331, dated Apr. 4, 2018, 48 pgs.
Grube, Eberhard et al., "Percutaneous Implantation of the CoreValve Self-Expanding Valve Prosthesis in High-Risk Patients With Aortic Valve Disease", *Circulation of the American Heart Disease*, vol. 114, 2006, pp. 1616-1624.
*Cath Lab Digest*, "Percutaneous Aortic Valve replacement with a Self-Expanding Stent: The CoreValve ReValving™ Procedure", talks with founder Dr. Jacques R. Seguin, Nov. 2004, pp. 26 and 28.
Jilaihawi et al., "Self-Expanding Percutaneous Aortic Valve Implantation", *Cardiac Interventions Today*, 2009, pp. 43-49.
Shultz, Carl J. et al., "Geometry and Degree of Apposition of the CoreValve ReValving System With Multislice Computed Tomography After Implantation in Patients With Aortic Stenosis", *Journal of the American College of Cardiology*, vol. 54, No. 10, 2008, pp. 911-918.
Padala, Muralidhar et al., "An Engineering Review of Transcatheter Aortic Valve Technologies", *Cardiovascular Engineering and Technology*, vol. 1, No. 1, 2010, pp. 77-87.
Popma, Jeffrey J. et al., "TAVI Using the CoreValve Revalving System, An Update on device data and the latest findings.", *Cardiac Interventions Today*, Jul./Aug. 2010, pp. 44-51.
Cribier, Alain et al., "Transcatheter Aortic and Mitral Valve Update, The progress and promise of valvular interventions.", *Cardiac Interventions Today*, Jul./Aug. 2010, pp. 35-49.
Grube, Eberhard et al., "Percutaneous Aortic Valve Replacement, An update on the current state of the CoreValve device.", *Cardiac Interventions Today*, May/Jun. 2008, pp. 27-30.
Green, Jacob et al., "Percutaneous Aortic Valve Replacement", An overview of catheter-based applications., *Cardiac Interventions Today*, Jun. 2007, pp. 29-32.
Dave, Rajesh M. et al, "Aortic Valvuloplasty, The state of the art and an introduction to percutaneous aortic valve technology.", *Cardiac Interventions Today*, Jun. 2007, pp. 51-59.
Feldman, Ted et al., "Prospects for Percutaneous Valve Therapies", *American Heart Association*, Circulation vol. 116, 2007, pp. 2866-2877.
Medgaget, "Medtronic's CoreValve Transcatheter Aortic Valve Replacement System Performs Well in Trial", May 20, 2009, 2 pgs.
Dvir, Danny et al., "Percutaneous Aortic Valve Implantation: Early Clinical Experience and Future Perspectives", IMAJ, vol. 11. Apr. 2009, pp. 244-249.
Chiam, Paul T et al., "Percutaneous Transcatheter Aortic Valve Implantation: Assessing Results, Judging Outcomes, and Planning Trials", JACC: Cardiovascular Interventions, vol. 1, No. 4, 2008, pp. 341-350.
Appeal Brief filed in U.S. Appl. No. 13,286,407, dated Aug. 21, 2014, 37 pgs.
Examiner's Answer to Appeal Brief filed in U.S. Appl. No. 13,286,407, dated Dec. 2, 2014, 9 pgs.
Reply Brief filed in U.S. Appl. No. 13,286,407, dated Feb. 3, 2015, 9 pgs.
Patent Board Decision for U.S. Appl. No. 13,286,407, dated Oct. 26, 2017, 14 pgs.
Request for Rehearing of Patent Board Decision, dated Dec. 22, 2017, 16 pgs.
Decision of Reconsideration Denied, dated Apr. 4, 2018, 12 pgs.
Decision by CAFC, dated Sep. 6, 2018, 2 pgs.
Decision of European Patent Opposition for EP 11 275 139.1, dated Nov. 14, 2019, 26 pgs.
Decision of European Patent Opposition as rendered for EP 11 275 139.1, dated Nov. 14, 2019, 20 pgs.
The Minutes of the Oral Proceedings before the Opposition Division on Oct. 21, 2019 for EP 11 275 139.1, dated Nov. 14, 2019, 30 pgs.

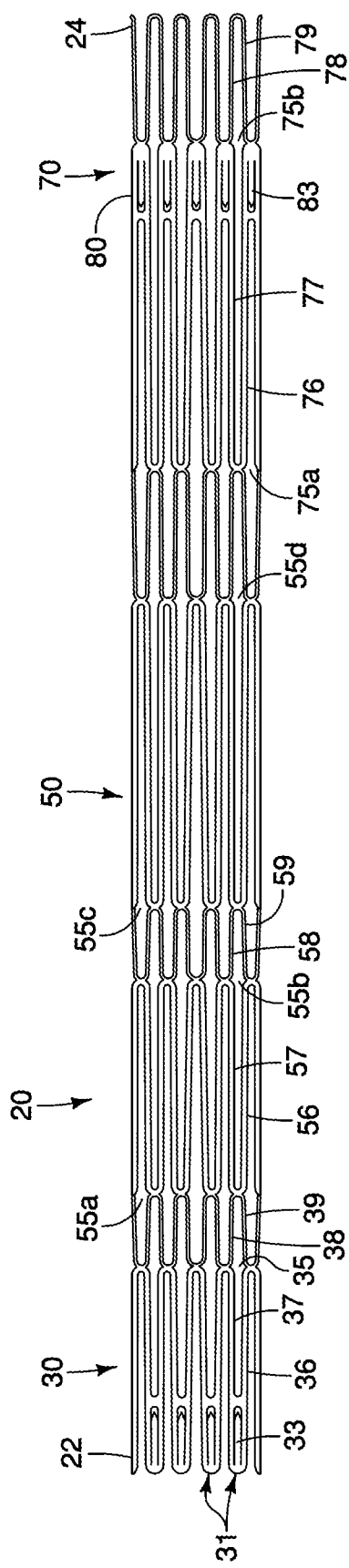
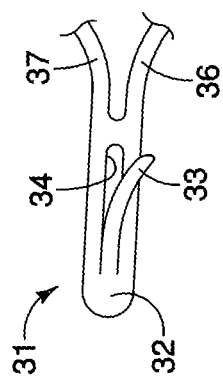
FIG. 3
FIG. 4

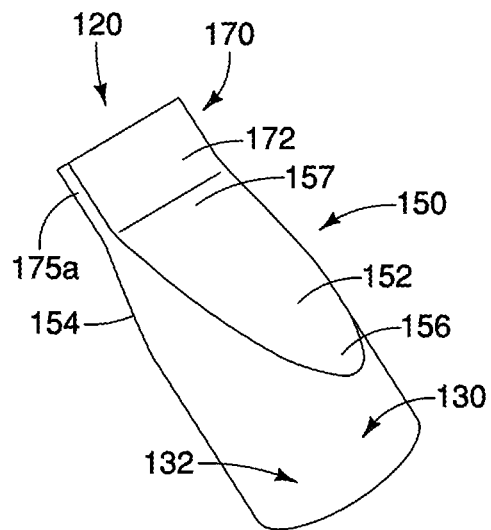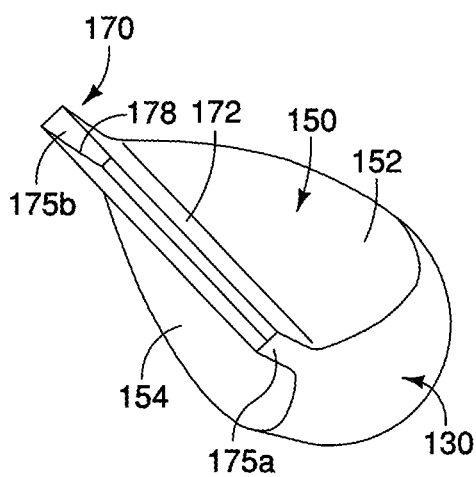
FIG. 5     FIG. 6
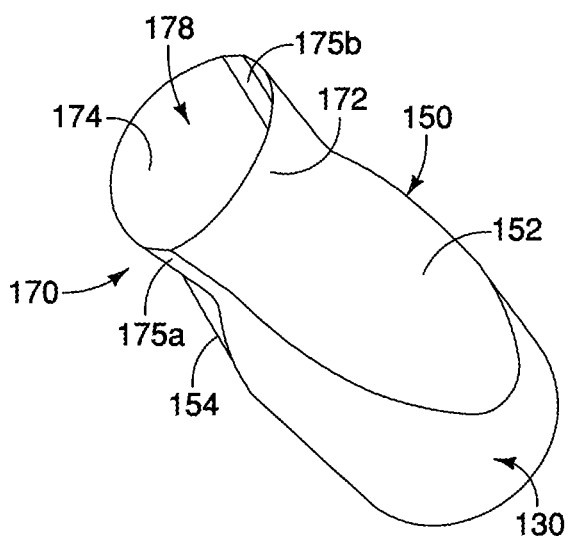
FIG. 7

STENT STRUCTURES FOR USE WITH VALVE REPLACEMENTS

PRIORITY CLAIM

The present patent document is a continuation application that claims the benefit of priority under 35 U.S.C. § 120 of U.S. patent application Ser. No. 13/286,407, filed Nov. 1, 2011, which claims priority to U.S. Provisional Patent Application Ser. No. 61/410,540 filed Nov. 5, 2010, each of which are hereby incorporated by reference in their entirety.

BACKGROUND

The present embodiments relate to implantable medical devices, and more particularly to an implantable medical device for the repair of a damaged endoluminal valve, such as an aortic valve.

The aortic valve functions as a one-way valve between the heart and the rest of the body. Blood is pumped from the left ventricle of the heart, through the aortic valve, and into the aorta, which in turn supplies blood to the body. Between heart contractions the aortic valve closes, preventing blood from flowing backwards into the heart.

Damage to the aortic valve can occur from a congenital defect, the natural aging process, and from infection or scarring. Over time, calcium may build up around the aortic valve causing the valve not to open and close properly. Certain types of damage may cause the valve to "leak," resulting in "aortic insufficiency" or "aortic regurgitation." Aortic regurgitation causes extra workload for the heart, and can ultimately result in weakening of the heart muscle and eventual heart failure.

After the aortic valve becomes sufficiently damaged, the valve may need to be replaced to prevent heart failure and death. One current approach involves the use of a balloon-expandable stent to place an artificial valve at the site of the defective aortic valve. Another current approach involves the positioning of an artificial valve at the site of the aortic valve using a self-expanding stent. The normal aortic valve functions well because it is suspended from above through its attachment to the walls of the coronary sinus in between the coronary orifices, and it has leaflets of the perfect size and shape to fill the space in the annulus. However, these features may be difficult to replicate with an artificial valve. The size of the implantation site depends on the unpredictable effects of the balloon dilation of a heavily calcified native valve and its annulus. Poor valve function with a persistent gradient or regurgitation through the valve may result. In addition, different radial force considerations may be needed at the different locations for the prosthesis to optimally interact with a patient's anatomy. Still further, it is important to reduce or prevent in-folding or "prolapse" of an artificial valve after implantation, particularly during diastolic pressures.

SUMMARY

The present embodiments provide a medical device for implantation in a patient. The medical device comprises a stent and a valve. The stent comprises a proximal region comprising a cylindrical shape having a first outer diameter when the stent is in an expanded state, and a distal region comprising a cylindrical shape having a second outer diameter when the stent is in the expanded state. The second outer diameter is greater than the first outer diameter.

In one embodiment, a plurality of closed cells are disposed around the perimeter of the proximal region of the stent, and another plurality of closed cells are disposed around the perimeter of the distal region of the stent. An overall length of each of the closed cells of the proximal region of the stent is less than an overall length of each of the closed cells of the distal region of the stent when the stent is in the expanded state.

In one embodiment, the stent further comprises a tapered region disposed between the proximal and distal regions. The tapered region transitions the stent from the first diameter to the second diameter. The tapered region further comprises a plurality of closed cells. An overall length of each of the closed cells of the tapered region is greater than the overall length of each of the closed cells of the proximal region and less than the overall length of each of the closed cells of the distal region when the stent is in the expanded state.

A proximal region of the valve is at least partially positioned within the proximal region of the stent, and the distal region of the valve is at least partially positioned within one of the tapered and distal regions of the stent. When implanted, the proximal region of the stent and the proximal region of the valve are aligned with a native valve, and the distal region of the valve is distally spaced-apart from the native valve.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 3 is a side view illustrating the stent structure of FIGS. 1-2 in a compressed state.

FIG. 4 is a side view of an exemplary integral barb of the stent structure of FIGS. 1-2.

FIGS. 5-6 are perspective views of an exemplary aortic valve when no forces are imposed upon the valve.

FIG. 7 is a perspective view the aortic valve of FIGS. 5-6 during systole.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
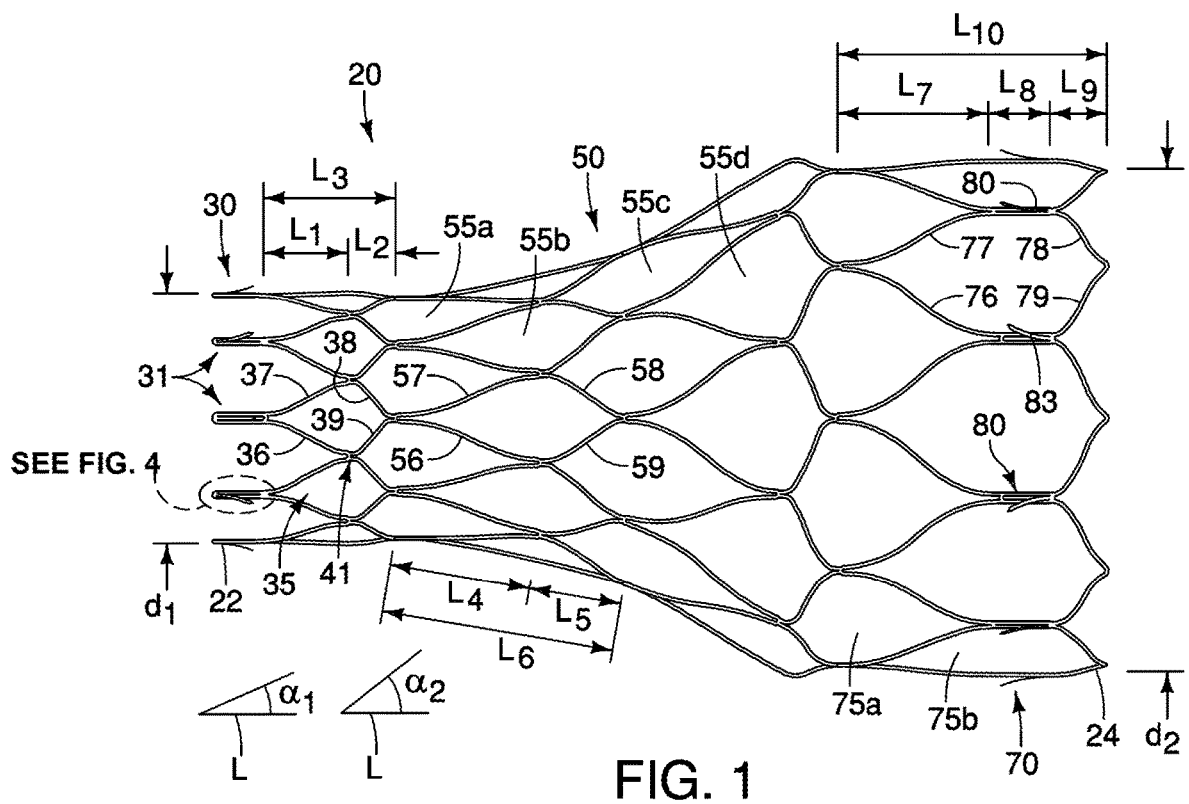
FIGS. 1-2 are, respectively, side and perspective views of an exemplary stent structure in an expanded state.
Figure 2:
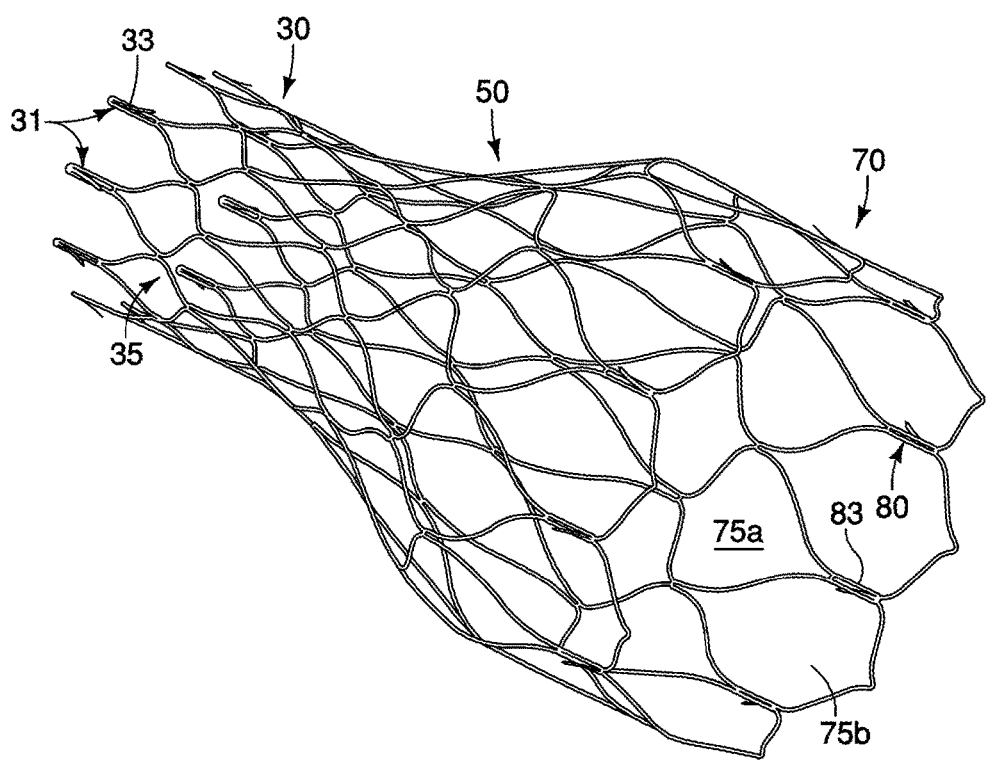
Figure 9:
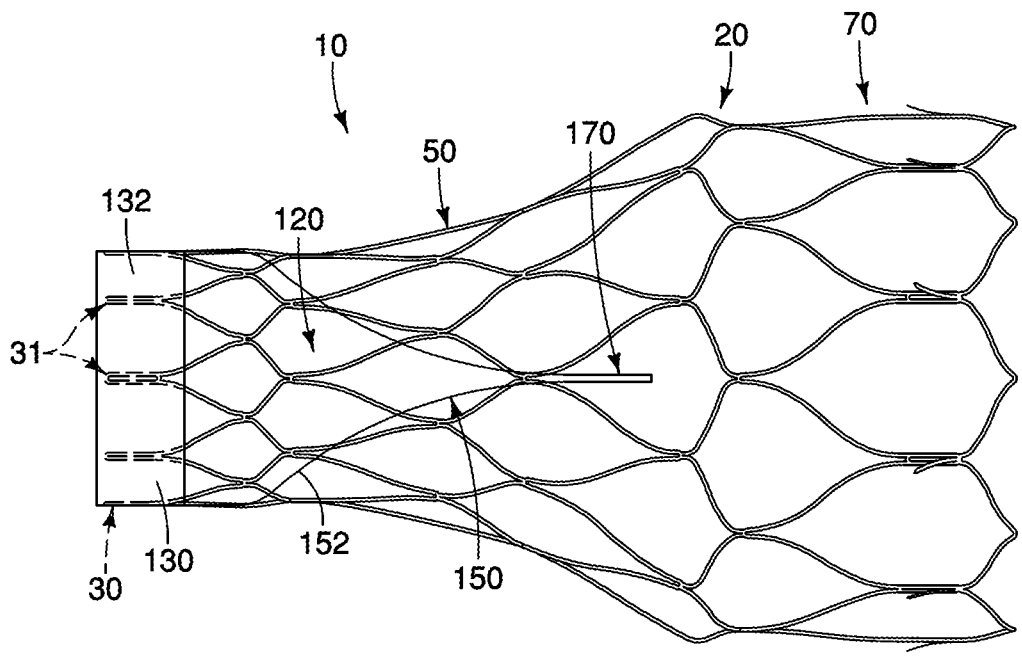

Referring now to FIGS. 1-2, a first embodiment of a stent structure 20, which may be used in conjunction with an aortic valve prosthesis, is shown and described. The stent structure 20 may be used in conjunction with an aortic valve 120 to form a completed aortic valve prosthesis 10 as shown in FIG. 9 below.

The stent structure 20 has a collapsed delivery state and an expanded deployed state, and generally comprises a proximal region 30, a tapered region 50, and a distal region 70, as shown in FIGS. 1-2. A pattern of the stent structure 20, depicted in a flattened and collapsed state, is shown in FIG. 3.

The stent structure 20 may be manufactured from a continuous cylinder into which a pattern may be cut by a laser or by chemical etching to produce slits in the wall of the cylinder. The resulting structure may then be heat set to give it a desired final configuration. As shown in FIGS. 1-2, the final configuration may include a shape having a series of multiple closed cells.

Figure 10:
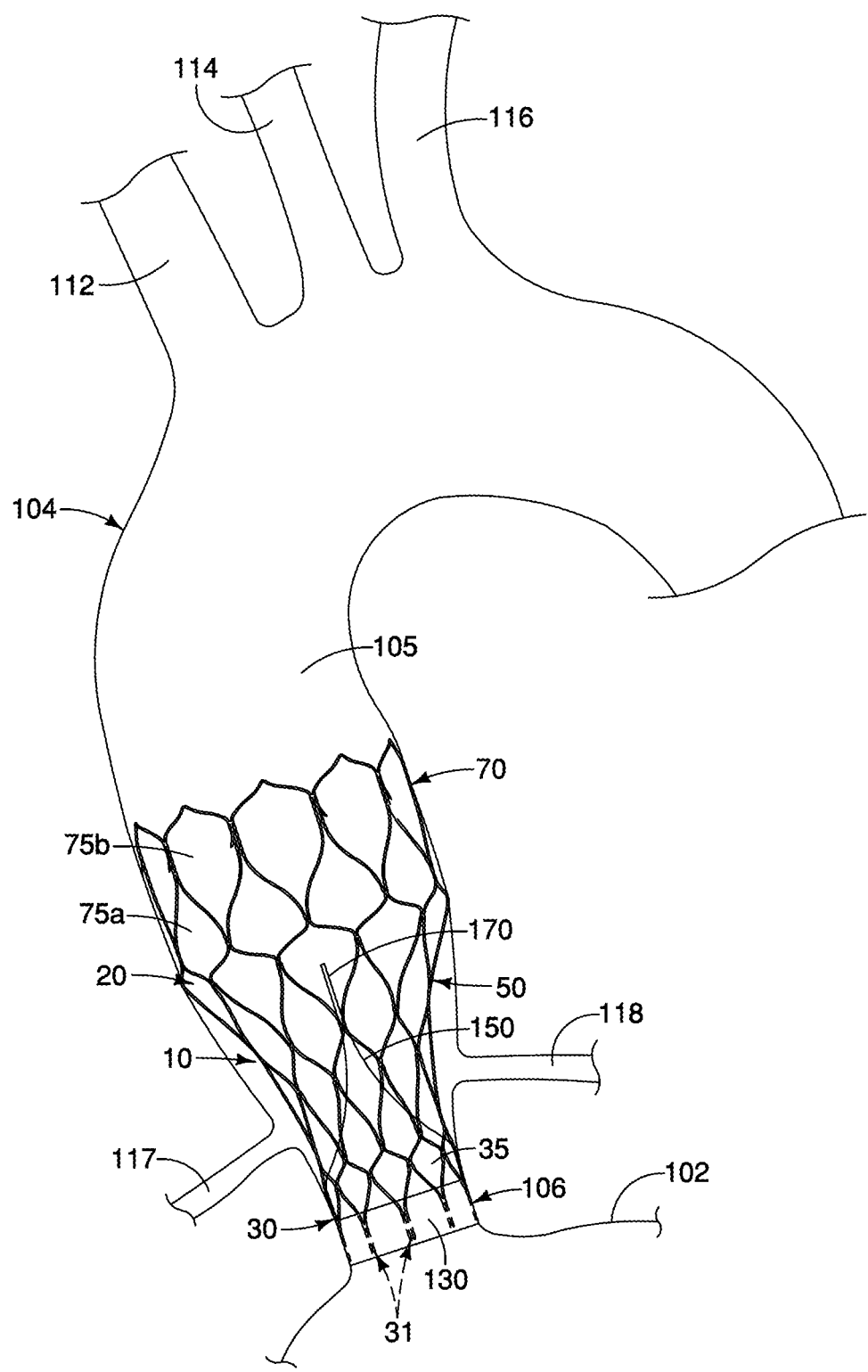
FIG. 10 is a schematic showing the aortic prosthesis of FIG. 9 disposed within a patient's anatomy.

The proximal region 30 of the stent structure 20 comprises a generally cylindrical shape having an expanded outer diameter $d_1$. The proximal region 30 is configured to be disposed at least partially within the aortic sinus, as shown in FIG. 10 below. By contrast, the distal region 70 of the stent structure 20 comprises a generally cylindrical shape having an expanded outer diameter $d_2$, and is configured to be disposed at least partially within the ascending aorta. The tapered region 50 generally bridges the change from diameter $d_1$ to diameter $d_2$.

The proximal region 30 of the stent structure 20 may comprise multiple adjacent proximal apices 31. Each proximal apex 31 may comprise an end region 32 having an integral barb 33 formed therein, as shown in FIG. 4. The barb 33 may be formed by laser cutting a desired barb shape into the end regions 32. A slit 34 therefore is formed into each end region 32 after the desired barb shape is formed, as shown in FIG. 4. Once the desired barb shape is cut, a main body of the barb 33 may be bent in a radially outward direction with respect to the end region 32. The angle may comprise any acute angle, or alternatively may be substantially orthogonal or obtuse. If desired, the barb 33 may be sharpened, for example, by grinding the tip of the barb, to facilitate engagement at a target tissue site.

Referring still to FIGS. 1-2, the proximal region 30 of the stent structure 20 further may comprise a plurality of closed cells 35 formed by multiple angled strut segments. In one example, four angled strut segments 36, 37, 38 and 39 form one closed cell 35, as shown in FIG. 1. In this example, a first proximal apex 31 extends distally and splits into first and second angled strut segments 36 and 37, respectively, which are joined to one another at a junction 41. Further, third and fourth angled strut segments 38 and 39 are joined at the junction 41 and extend distally therefrom, as shown in FIG. 1. In a compressed state, the angled strut segments 36-39 of the cell 35 may be compressed such that they are substantially parallel to one another.

The first and second angled strut segments 36 and 37 each generally comprise a length $L_1$, and each are generally disposed at an angle $\alpha_1$ relative to a longitudinal axis L of the stent structure 20, as shown in FIG. 1. The third and fourth angled strut segments 38 and 39 each generally comprise a length $L_2$ and each are generally disposed at an angle $\alpha_2$ relative to the longitudinal axis L, as shown in FIG. 1. The closed cell 35 comprises a total length $L_3$, representing the combined lengths $L_1$ and $L_2$, as shown in FIG. 1.

In this example, the length $L_1$ of the first and second angled strut segments 36 and 37 is greater than the length $L_2$ of the third and fourth angled strut segments 38 and 39. In one embodiment, the length $L_1$ may be about 1.5 to about 4.0 times greater than the length $L_2$.

Moreover, a cross-sectional area of the first and second angled strut segments 36 and 37 may be greater than a cross-sectional area of the third and fourth angled strut segments 38 and 39. In one embodiment, the cross-sectional area of the first and second angled strut segments 36 and 37 is about 4 times greater than the cross-sectional area of the third and fourth angled strut segments 38 and 39. The increased cross-sectional area of the first and second angled strut segments 36 and 37 causes these segments to primarily provide the radial force within the closed cells 35, while the third and fourth angled strut segments 38 and 39 are mainly intended for connecting adjacent closed cells 35 and 55a, instead of providing significant radial force.

Further, in this example, the angle $\alpha_2$ of the third and fourth angled strut segments 38 and 39 is greater than the angle $\alpha_1$ of the first and second angled strut segments 36 and 37. Since the first and second angled strut segments 36 and 37 are primarily providing the radial force, the angle $\alpha_1$ is selected to achieve the desired radial force, while as noted above, the third and fourth angled strut segments 38 and 39 are mainly intended for connecting adjacent closed cells 35 and 55a, and therefore yield a different angle $\alpha_2$ for this different primary purpose. In one embodiment, the angle $\alpha_2$ may be about 1.2 to 4.0 times greater than the angle $\alpha_1$.

Overall, given the relative lengths and angle configurations described above, each closed cell 35 comprises a generally spade-shaped configuration, as shown in FIGS. 1-2. As will be apparent, however, the relative lengths and angles may be greater or less than depicted and/or provided in the exemplary dimensions disclosed herein.

The pattern of angled strut segments 36-39 may be repeated around the circumference of the proximal region 30 of the stent structure 20. In this manner, the stent structure 20 may be formed into a continuous, generally cylindrical shape. In one example, ten proximal apices 31 and ten closed cells 35 are disposed around the circumference of the proximal region 30, although greater or fewer proximal apices and closed cells may be provided to vary the diameter and/or radial force characteristics of the stent.

The proximal region 30 may be flared slightly relative to the longitudinal axis L. In one example, a proximal end of each apex 31 may be bowed outward relative to a distal end of the same apex 31. Such a flaring may facilitate engagement with the aortic sinus when implanted.

Referring still to FIGS. 1-2, the tapered region 50 also comprises a plurality of closed cells. In this example, four different closed cells 55a, 55b, 55c and 55d are provided along the length of the tapered region 50. Each of the closed cells 55a-55d may comprise a slightly different shape, as shown in FIGS. 1-2. In this example, ten of each series of closed cells 55a-55d are disposed around the circumference of the tapered region 50, and the diameter of the tapered region 50 increases from the outer diameter $d_1$ to the outer diameter $d_2$.

In one example, four angled strut segments 56, 57, 58 and 59 form one closed cell 55b, as shown in FIG. 1. The first and second angled strut segments 56 and 57 each generally comprise a length $L_4$ and each are generally disposed at an angle relative to the longitudinal axis L that may be about the same as, or slightly greater or less than, the angle $\alpha_1$. The third and fourth angled strut segments 58 and 59 each generally comprise a length $L_5$ and each are generally disposed at an angle relative to the longitudinal axis L that may be about the same as, or slightly greater or less than, the angle $\alpha_2$. The closed cell 55b comprises a total length $L_6$, representing the combined lengths $L_4$ and $L_5$, as shown in FIG. 1.

In this example, the length $L_4$ of the first and second angled strut segments 56 and 57 is greater than the length $L_5$ of the third and fourth angled strut segments 58 and 59. In one embodiment, the length $L_4$ may be about 1.1 to about 4 times greater than the length $L_5$.

Further, in this example, the total length $L_6$ of the closed cell 55b of the tapered region 50 is greater than the total length $L_3$ of the closed cell 35 of the proximal region 30, as shown in FIG. 1. Moreover, in one example, the length of one or more individual struts of the tapered region 50, e.g., first and second angled strut segments 56 and 57 having length $L_4$, may be longer than the total length $L_3$ of the closed cell 35 of the proximal region 30.

The distal region 70 similarly comprises a plurality of closed cells. In this example, two different closed cells 75a and 75b are provided along the length of the distal region 70. The closed cells 75a and 75b may comprise a different shape relative to one another, as shown in FIGS. 1-2. In this example, ten of each series of closed cells 75a and 75b are disposed around the circumference of the distal region 70 to form the overall outer diameter $d_2$.

In one example, the most distal closed cell 75b comprises four angled strut segments 76, 77, 78 and 79, as shown in FIG. 1. The first and second angled strut segments 76 and 77 each generally comprise a length $L_7$ and each are generally disposed at an angle relative to the longitudinal axis L that may be about the same as, or slightly greater or less than, the angle $\alpha_1$. The third and fourth angled strut segments 78 and 79 each generally comprise a length $L_9$ and each are generally disposed at an angle relative to the longitudinal axis L that may be about the same as, or slightly greater or less than, the angle $\alpha_2$.

Further, a barbed region 80 having a barb 83 is disposed between the angled strut segments, as shown in FIG. 1. The barb 83 of the barbed region 80 may be formed integrally in the same manner as the barb 33 of the proximal region 30, as shown in FIG. 4, but preferably faces in a proximal direction. The barbed region 80 is generally parallel to the longitudinal axis L of the stent structure 20 and comprises a length $L_8$. The cell 55b comprises a total length $L_{10}$, representing the combined lengths $L_7$, $L_8$ and $L_9$, as shown in FIG. 1.

In this example, the length $L_7$ of the first and second angled strut segments 76 and 77 is greater than the length $L_9$ of the third and fourth angled strut segments 78 and 79. In one embodiment, the length $L_7$ may be about 1.1 to about 4.0 times greater than the length $L_9$.

Further, in this example, the total length $L_{10}$ of the closed cell 75b of the distal region 70 is greater than the total length $L_6$ of the closed cell 55b of the tapered region 50, which in turn is greater than the total length $L_3$ of the closed cell 35 of the proximal region 30, as shown in FIG. 1. Therefore, the lengths of individual closed cells increase along the stent structure from a proximal end 22 to a distal end 24 of the stent structure 20.

Advantageously, since the lengths of individual closed cells generally increase along the stent structure 20 from the proximal end 22 to the distal end 24, the forces imposed by the stent structure 20 along different regions may be varied for a patient's anatomy. Radial force and stiffness are a function of the individual cell lengths. Therefore, in the example of an aortic valve replacement, a relatively short length $L_3$ of the closed cell 35 of the proximal region 30 yields a relatively high radial force imposed upon the aortic sinus to allow for an enhanced and rigid attachment at this location. Conversely, a relatively long length $L_{10}$ of the closed cell 75b of the distal region 70 yields a relatively low radial force imposed upon the ascending aorta, thereby facilitating a flexible contour at the distal region 70 that does not adversely impact the ascending aorta 105.

Additionally, radial force and stiffness are a function of the strut angles. In the example of FIGS. 1-2, the individual struts 36 and 37 of the proximal region 30 may have a shallower strut angle relative to the individual struts 76 and 77 of the distal region 70, i.e., the individual struts 36 and 37 may be more perpendicular to the longitudinal axis L of the device. Therefore, the angles of the individual struts 36 and 37 may contribute to a higher radial force at the proximal region 30 relative to the individual struts 76 and 77 of the distal region 70.

Further, an increased strut width may be provided at the proximal region 30 to promote a higher radial force relative to the strut width at the distal region 70. In sum, the stent structure 20 has different radial force properties at its proximal and distal regions 30 and 70 that beneficially interact with their associated regions into which they are implanted, e.g., the aortic sinus and the ascending aorta, respectively.

In one embodiment, the lengths of individual cells may always increase relative to one another moving in a proximal to distal direction, i.e., each closed cell has an overall length that is greater than a length of every other closed cell that is disposed proximally thereof. In other embodiments, adjacent cells may comprise about the same length, or a proximal cell may comprise a lesser length than an adjacent distal cell. Therefore, while the lengths of individual angled strut segments generally increase in a proximal to distal direction, it is possible that some of the individual angled strut segments of a more distal region may be smaller than a more proximally oriented region.

Expansion of the stent structure 20 is at least partly provided by the angled strut segments, which may be substantially parallel to one another in a compressed state of FIG. 3, but may tend to bow outward away from one another in the expanded state shown in FIGS. 1-2. The stent structure 20 may be formed from any suitable material, and formed from a laser-cut cannula. The stent structure 20 has a reduced diameter delivery state so that it may be advanced to a target location within a vessel or duct. Further, the struts of the stent may comprise a substantially flat wire profile or may comprise a rounded profile. As best seen in FIGS. 1-2, the struts of the stent generally comprise a flat wire profile in this example.

The stent structure 20 may be manufactured from a super-elastic material. Solely by way of example, the super-elastic material may comprise a shape-memory alloy, such as a nickel titanium alloy (nitinol). If the stent structure 20 comprises a self-expanding material such as nitinol, the stent may be heat-set into the desired expanded state, whereby the stent structure 20 can assume a relaxed configuration in which it assumes the preconfigured first expanded inner diameter upon application of a certain cold or hot medium. Alternatively, the stent structure 20 may be made from other metals and alloys that allow the stent structure 20 to return to its original, expanded configuration upon deployment, without inducing a permanent strain on the material due to compression. Solely by way of example, the stent structure 20 may comprise other materials such as stainless steel, cobalt-chrome alloys, amorphous metals, tantalum, platinum, gold and titanium. The stent structure 20 also may be made from non-metallic materials, such as thermoplastics and other polymers.

It is noted that some foreshortening of the stent structure 20 may occur during expansion of the stent from the collapsed configuration of FIG. 3 to the expanded deployed state of FIGS. 1-2. Since the proximal region 30 of the stent structure 20 is deployed first, it is expected that such foreshortening is not problematic since a precise landing area of the distal region 70 within the ascending aorta is generally not needed, so long as solid contact is achieved.

Moreover, in order to reduce migration of the stent structure when implanted at a target site, it is preferred that the barbs 33 of the proximal region 30 are oriented in a distally-facing direction, whereas the barbs 83 of the distal region 70 are oriented in a proximally-facing direction. However, additional or fewer barbs may be disposed at various locations along the stent structure 20 and may be oriented in the same or different directions. Moreover, integral and/or externally attached barbs may be used.

Referring now to FIGS. 5-7, a first embodiment of an aortic valve 120, which may be used in conjunction with the stent structure 20 to form an aortic prosthesis, is shown and described. The aortic valve 120 generally comprises proximal and distal regions 130 and 170, respectively, and a tapered region 150 disposed therebetween. The aortic valve 120 comprises a delivery state in which it may be compressed for percutaneous implantation along with the stent structure 20, and further comprises different states during systole and diastole. Generally, antegrade flow opens the aortic valve 120 while retrograde flow closes the aortic valve 120. In the phase of systole for the aortic valve 120, depicted in FIG. 7, blood may flow through the opposing flat surfaces 172 and 174 at the distal end 170 of the aortic valve 120. In the phase of diastole for the aortic valve 120, opposing flat surfaces 172 and 174 at the distal end 170 of the aortic valve 120 are generally adjacent to one another to inhibit blood flow back through the valve.

The proximal region 130 generally comprises a cylindrical body having an outer diameter that is approximately equal to, or just less than, an expanded inner diameter of the proximal region 30 of the stent structure 20. In one method of manufacture, shown in FIGS. 8-9 and described below, the aortic valve 120 is disposed generally within the stent structure 20 such that the proximal region 130 is at least partially aligned with the proximal region 30 of the stent structure 20.

The tapered region 150 of the aortic valve 120 may comprise two opposing flat surfaces 152 and 154, as shown in FIGS. 5-6. The opposing flat surfaces 152 and 154 generally each comprise a proximal portion 156 in the form of a curved area that reduces the diameter of the proximal region 130, and a distal portion 157 in the form of a wide flat panel that transitions into the distal region 170, as shown in FIGS. 5-6.

The distal region 170 of the aortic valve 120 may comprise a generally rectangular profile from an end view, i.e., looking at the device from a distal to proximal direction. The distal region 170 comprises the opposing flat surfaces 172 and 174 noted above, which are separated by narrower flat sides 175a and 175b, as shown in FIGS. 5-6. The opposing flat surfaces 152 and 154 of the tapered region 150 generally transition into the opposing flat surfaces 172 and 174 of the distal region 170, respectively. The opposing flat surfaces 152 and 154 of the tapered region 150 are angled relative to both the proximal region 130 and the distal region 170, as shown in FIGS. 5-6.

The aortic valve 120 may comprise a biocompatible graft material is preferably non-porous so that it does not leak under physiologic forces. The graft material may be formed of Thoralon® (Thoratec® Corporation, Pleasanton, Calif.), Dacron® (VASCUTEK® Ltd., Renfrewshire, Scotland, UK), a composite thereof, or another suitable material. Preferably, the graft material is formed without seams. The tubular graft can be made of any other at least substantially biocompatible material including such fabrics as other polyester fabrics, polytetrafluoroethylene (PTFE), expanded PTFE, and other synthetic materials. Naturally occurring biomaterials are also highly desirable, particularly a derived collagen material known as extracellular matrix. An element of elasticity may be incorporated as a property of the fabric or by subsequent treatments such as crimping.

Figure 8:
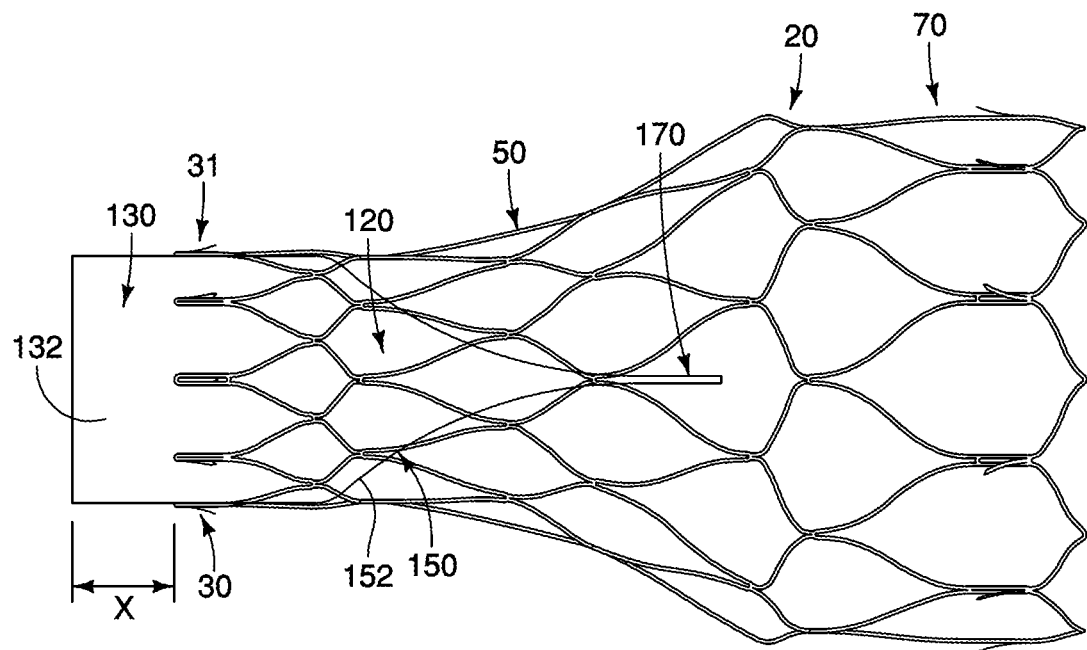
FIGS. 8-9 are side views illustrating a technique for coupling the aortic valve of FIGS. 5-7 to the stent structure of FIGS. 1-3.

Referring to FIGS. 8-9, in one method of manufacture, the aortic valve 120 is disposed generally within the stent structure 20 such that the proximal region 130 of the aortic valve 120 is at least partially aligned with the proximal region 30 of the stent structure 20. A proximal attachment portion 132 of the aortic valve 120 having a length x is disposed proximal to the proximal apices 31 of the stent structure 20, as shown in FIG. 8, then the proximal attachment portion 132 is folded externally over the proximal apices 31, as shown in FIG. 9. The proximal attachment portion 132 then may be sutured or otherwise attached to the proximal apices 31 and/or any of the angled strut segments 36-39, thereby securing a portion of the aortic valve 120 to the stent structure 20 to form a complete aortic prosthesis 10, as depicted in FIG. 9. The barbs 33 of the stent structure 20 may protrude through the fabric of the proximal attachment portion 132 for engagement with targeted tissue.

When the aortic valve 120 is coupled to the stent structure 20 as shown in FIGS. 8-9, the distal region 170 of the aortic valve 120 may extend within the tapered region 50 and/or the distal region 70 of the stent structure 20, and may be generally centrally disposed therein, although the exact positioning of distal region 170 of the aortic valve 120 relative to the stent structure 20 may be varied as needed. Moreover, one or more reinforcement members, described generally in FIGS. 11-19 below, may be coupled to the aortic valve 120 and/or the stent structure 20 to enhance structural integrity and/or functionality of the aortic prosthesis 10.

Advantageously, the distal region 170 of the aortic valve 120 is disposed within the tapered region 50 and/or the distal region 70 of the stent structure 20, which are positioned in the proximal ascending thoracic aorta above (distal to) the annulus and above the native aortic valve. Previous valves are designed to occupy the aortic annulus; however, the unpredictable shape and diameter of the aortic annulus makes the valve unpredictable in shape and diameter, leading to asymmetric replacement valve movement, leakage and reduced durability. In short, by moving the distal region 170 of the aortic valve 120 to a distally spaced-apart location relative to the native aortic valve, i.e., the unpredictable shape and diameter of the aortic annulus have less impact upon the spaced-apart distal region 170 of the aortic valve 120, and therefore the distal region 170 is less subject to asymmetric valve movement and leakage, and may have increased durability.

The shape and dimensions of the proximal and tapered regions 130 and 150 can vary without significantly affecting flow or valve function at the distal region 170. While the distal region 170 of the valve 120 is shown having a generally rectangular shape, a tricuspid-shaped distal region of the valve may be provided, in which case the tapered region 150 may be omitted or altered to accommodate such a tricuspid-shaped distal region.

Referring now to FIG. 10, a partial cut-away view of a heart 102 and an aorta 104 are shown. The heart 102 may comprise an aortic valve 106 that does not seal properly. This defect of the aortic valve 106 allows blood to flow from the aorta 104 back into the left ventricle, leading to a disorder known as aortic regurgitation. Also shown in FIG. 10 are a brachiocephalic trunk 112, a left common carotid artery 114, and a left subclavian artery 116. A portion of the aorta 104 referred to herein as an ascending aorta 105 is shown located between the aortic valve 106 and the brachiocephalic trunk 112. A patient's coronary arteries 117 and 118 are located distal to the aortic valve 106.

The aortic prosthesis 10 is introduced into a patient's vascular system, delivered, and deployed using a deployment device, or introducer. The deployment device delivers and deploys the aortic prosthesis 10 within the aorta at a location to replace the aortic valve 106, as shown in FIG. 10. The deployment device may be configured and sized for endoluminal delivery and deployment through a femoral cut-down. The aortic prosthesis 10, with the stent structure 20 in a radially collapsed state, may be inserted into a delivery catheter using conventional methods. In addition to a delivery catheter, various other components may need to be provided in order to obtain a delivery and deployment system that is optimally suited for its intended purpose. These include and are not limited to various outer sheaths, pushers, trigger wires, stoppers, wire guides, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments.

In one aspect, a trigger wire release mechanism is provided for releasing a retained end of the stent structure 20 of the aortic prosthesis 10. Preferably, the trigger wire arrangement includes at least one trigger wire extending from a release mechanism through the deployment device, and the trigger wire is engaged with selected locations of the stent structure 20. Individual control of the deployment of various regions of the stent structure 20 enables better control of the deployment of the aortic prosthesis 10 as a whole.

While the stent structure 20 is generally described as a self-expanding framework herein, it will be appreciated that a balloon-expandable framework may be employed to accomplish the same functionality. If a balloon-expandable stent structure is employed, then a suitable balloon catheter is employed to deliver the aortic prosthesis as generally outlined above. Optionally, after deployment of a self-expanding stent structure 20, a relatively short balloon expandable stent may be delivered and deployed inside of the proximal region 30 of the stent structure 20 to provided added fixation at the location of the aortic sinus.

Upon deployment, the aortic prosthesis 10 is positioned as generally shown in FIG. 10. Advantageously, as noted above, since the lengths of individual cells generally increase along the stent structure 20 from the proximal end 22 to the distal end 24, a relatively high radial force is imposed by the closed cells 35 of the proximal region 30 upon the aortic sinus 106 to allow for an enhanced and rigid attachment at this location. Conversely, a relatively low radial force is imposed by the closed cells 75a and 75b of the distal region 70 upon the ascending aorta 105, thereby facilitating a flexible contour at the distal region that does not adversely impact the ascending aorta 105.

When the aortic prosthesis 10 is implanted, sufficient flow into the coronary arteries 117 and 118 is maintained during retrograde flow. In particular, after blood flows through the distal region 170 of the aortic valve 120, blood is allowed to flow adjacent to the outside of the tapered central region 150 of the aortic valve 120 and into the coronary arteries 117 and 118, i.e., through the open individual cells of the stent structure 20.

Further, if the barbs 33 are disposed at the proximal region 30, the barbs 33 promote a secure engagement with the aortic sinus 106. Similarly, the barbs 83 at the distal region 70 promote a secure engagement with the ascending aorta 105. In the event barbs are omitted, the proximal and distal regions 30 and 70 may be configured so that the radial forces exerted upon the coronary sinus 105 and the ascending aorta 105, respectively, are enough to hold the stent structure 20 in place.

The shape, size, and dimensions of each of the members of the aortic prosthesis 10 may vary. The size of a preferred prosthetic device is determined primarily by the diameter of the vessel lumen (preferably for a healthy valve/lumen combination) at the intended implant site, as well as the desired length of the overall stent and valve device. Thus, an initial assessment of the location of the natural aortic valve in the patient is determinative of several aspects of the prosthetic design. For example, the location of the natural aortic valve in the patient will determine the dimensions of the stent structure 20 and the aortic valve 120, the type of valve material selected, and the size of deployment vehicle.

After implantation, the aortic valve 120 replaces the function of the recipient's native damaged or poorly performing aortic valve. The aortic valve 120 allows blood flow when the pressure on the proximal side of the aortic valve 120 is greater than pressure on the distal side of the valve. Thus, the artificial valve 120 regulates the unidirectional flow of fluid from the heart into the aorta.

Referring now to FIGS. 11-19, various reinforcement members are described that may be coupled to the aortic valve 120 and/or the stent structure 20 to enhance structural integrity and/or functionality of the aortic prosthesis 10. The normal, native aortic valve is suspended from above through its attachment to the walls of the coronary sinus, and suspended aortic valves resist the forces created by diastolic pressure on closed leaflets through attachment to downstream support. The various reinforcement members of FIGS. 11-19 are intended to reinforce the aortic valve 120, and in particular, prevent in-folding or "prolapse" of the valve during diastole.

Figure 11:
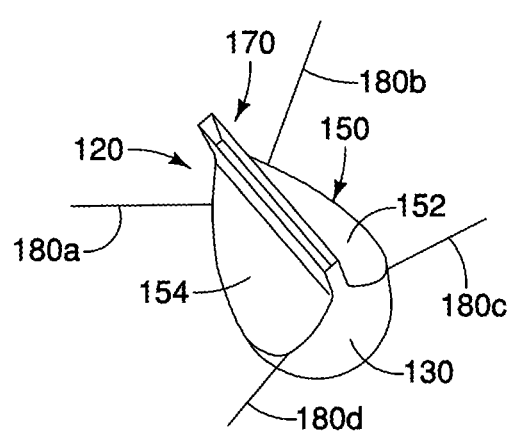
FIGS. 11-12 are, respectively, perspective views of an aortic valve comprising suspension ties when no forces are imposed and during diastole.
Figure 12:
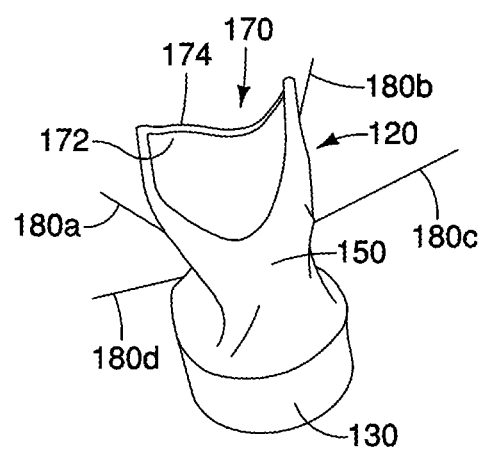
Figure 13:
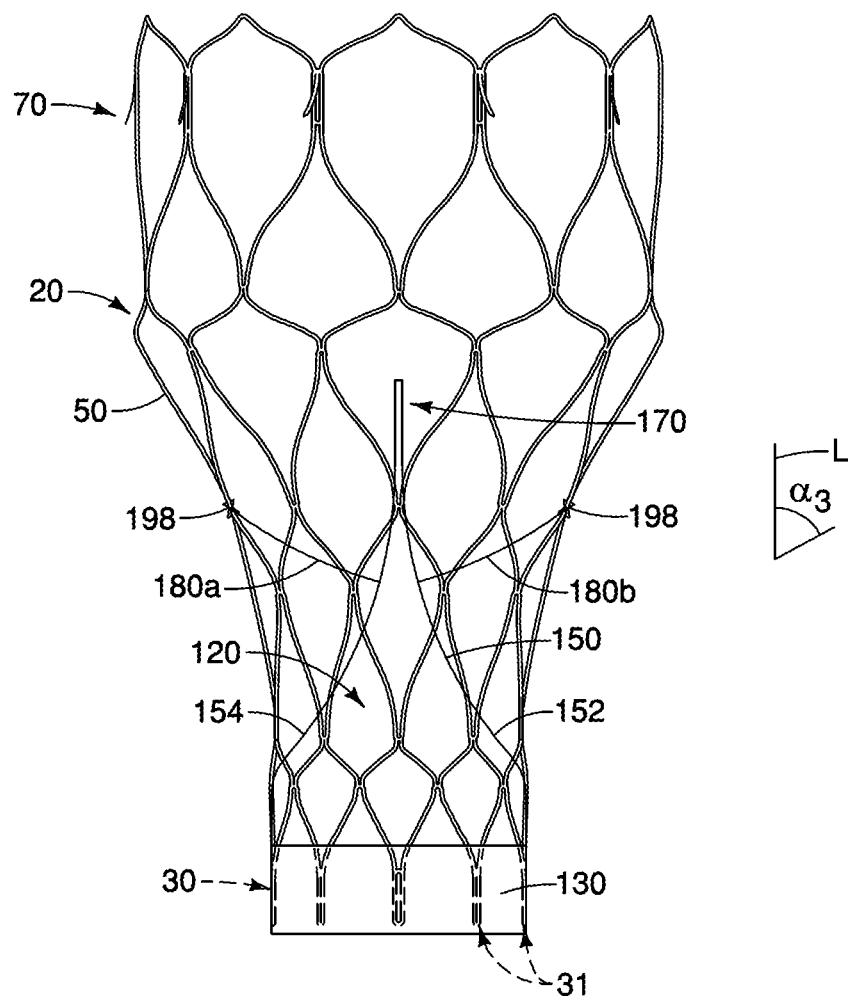
FIG. 13 is a side view illustrating coupling of the aortic valve of FIGS. 11-12 to the stent structure of FIGS. 1-3.

In FIGS. 11-13, a first embodiment of reinforcement members comprises a plurality of suspension ties 180a-180d that are coupled between the tapered region 150 of the aortic valve 120 and the tapered region 50 of the stent structure 20. In the phase of systole for the aortic valve 120, blood may flow through the opposing flat surfaces 172 and 174 at the distal end 170 of the aortic valve 120, and the suspension ties 180a-180d are relatively slack allowing for normal opening of the aortic valve 120. In the phase of diastole for the aortic valve 120, opposing flat surfaces 172 and 174 at the distal end 170 of the aortic valve 120 are generally adjacent to one another to inhibit blood flow back through the valve, while the suspension ties 180a-180d become more taut and prevent prolapse of the aortic valve 120 when retrograde flow is imposed upon the exterior surfaces of the valve, as depicted in the finite element analysis simulation of FIG. 12. In effect, the suspension ties 180a-180d advantageously provide a safety mechanism by which prolapse is avoided during retrograde flow.

In the example of FIGS. 11-13, the suspension ties 180a-180d may be molded into the aortic valve 120 in the manner that fiber reinforcements are molded into a graft structure, and further may be coupled to one or more struts of the stent structure 20 using sutures 198 or another suitable coupling member that does not impede expansion of the stent structure 20. While first ends of the suspension ties 180a-180d are shown coupled to the tapered region 150 of the aortic valve 120, they may alternatively, or additionally, be coupled to another location, such as the distal region 170. Similarly, while second ends of the suspension ties 180a-180d are shown coupled to the tapered region 50 of the stent structure 20, they may alternatively, or additionally, be coupled to another location, such as the distal region 70. While four exemplary suspension ties 180a-180d are shown, greater or fewer suspension ties may be used, and their positioning may be varied as noted above, to achieve the desired functionality and reduce potential prolapse of the aortic valve 120.

The angles $\alpha_3$ of the suspension ties 180a-180d relative to the longitudinal axis L, as shown in FIG. 13, may be between about 40-80 degrees when relatively slack. However, it will be appreciated the angles $\alpha_3$ may be greater or less than what is depicted in FIG. 13.

In one example, the suspension ties 180a-180d comprise a thickness of between about 0.002-0.02 inches, and are molded into a Thoralon® or Dacron® coating. Other materials may be used, so long as the suspension ties 180a-180d are non-thrombogenic, or coated with a non-thrombogenic material.

Advantageously, in the case where the tapered or distal regions 150 and 170 of the aortic valve 120 are supported from above through attachment to the stent structure 20 at a location in the ascending thoracic aorta, the aortic valve 120 can therefore be as long as necessary for optimal valve function, even if it is of a simple bicuspid design. In other words, the length of the aortic valve 120 can be varied such that the distal region 170 of the aortic valve 120 is positioned at the desired location within the ascending thoracic aorta spaced-apart from the native aortic annulus.

Figure 14:
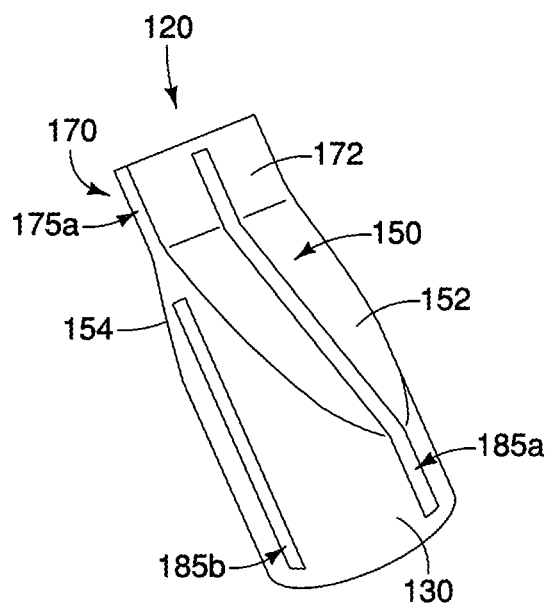
FIGS. 14-16 are, respectively, perspective views illustrating an aortic valve comprising reinforcement strips when no forces are imposed, during systole and during diastole.
Figure 15:
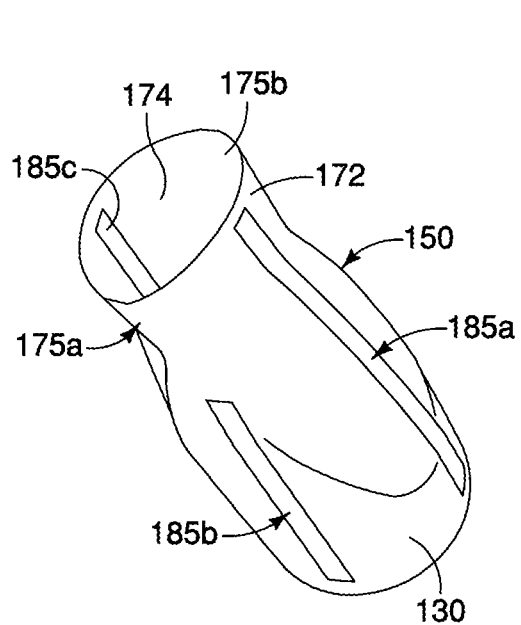
Figure 16:
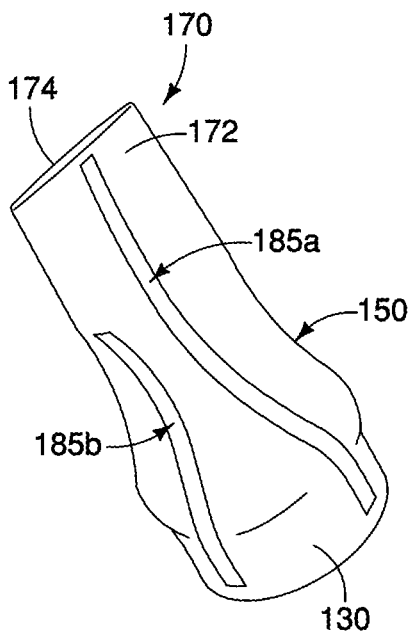

Referring now to FIGS. 14-19, alternative embodiments of reinforcement members are shown and described that comprise one or more reinforcement strips. In FIGS. 14-16, a first reinforcement strip 185a generally extends between a portion of the proximal region 130, through one opposing flat surface 152 of the tapered region 150, and to one opposing flat surface 172 of the distal region 170, as shown in FIGS. 14-16. A second reinforcement strip 185b is disposed about 90 degrees apart from the first reinforcement strip 185a, and generally extends between a portion of the proximal region 130 towards one of the narrower flat sides 175a. A third reinforcement strip 185c is disposed about 90 degrees apart from the first reinforcement strip 185a, and generally extends between a portion of the proximal region 130, through one opposing flat surface 154 of the tapered region 150, and to one opposing flat surface 174 of the distal region 170. A fourth reinforcement strip is obscured in FIGS. 14-16 but may be disposed about 90 degrees apart from the second reinforcement strip 185b and is a mirror image thereof.

In the phase of systole for the aortic valve 120, shown in FIG. 15, blood may flow through the opposing flat surfaces 172 and 174 at the distal end 170 of the aortic valve 120, and the reinforcement strips 185a-185c are relatively flat allowing for normal opening of the aortic valve 120. In the phase of diastole for the aortic valve 120, shown in FIG. 16, opposing flat surfaces 172 and 174 at the distal end 170 of the aortic valve 120 are generally adjacent to one another to inhibit blood flow back through the valve, while the reinforcement strips 185a-185d may become bowed radially inward along the tapered region 150 to prevent prolapse of the aortic valve 120 when retrograde flow is imposed upon the exterior surfaces of the valve. In one example, the reinforcement strips 185a-185c may snap between the states depicted in FIGS. 15-16 during systole and diastole, respectively, when the associated pressures are imposed upon the aortic valve 120. In effect, the reinforcement strips 185a-185c advantageously provide a safety mechanism by which prolapse is avoided during retrograde flow.

In one example, the reinforcement strips 185a-185c of FIGS. 14-16 comprise stainless steel or nitinol, though any suitable material to perform such functions may be used. The reinforcement strips may comprise a thickness of about 0.002 to about 0.010 inches and may be molded into the material of the aortic valve 120, or coupled externally thereto.

Figure 17:
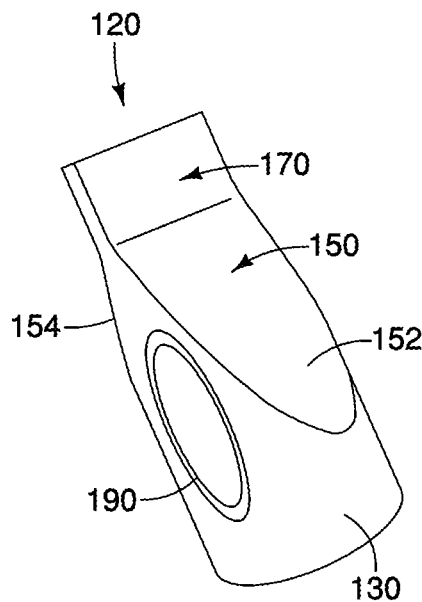
FIGS. 17-19 illustrate aortic valves comprising one or more alternative reinforcement strips.
Figure 18:
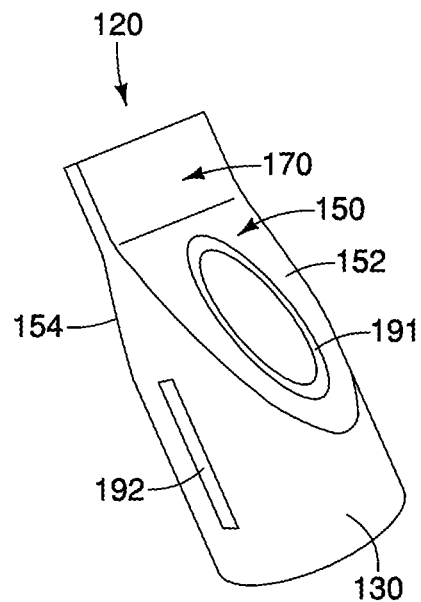
Figure 19:
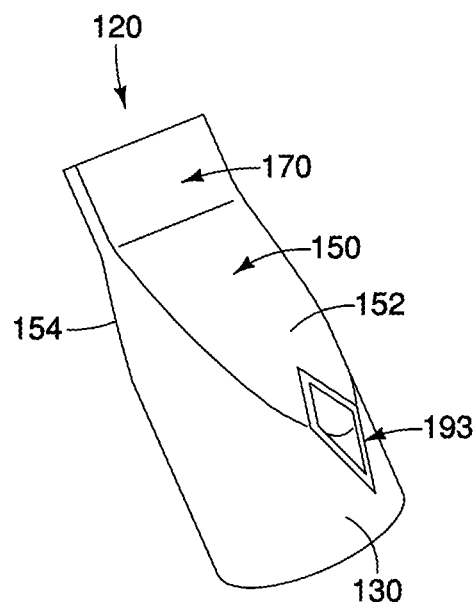

In FIGS. 17-19, various alternative reinforcement strips are depicted. In FIG. 17, at least one elliptical reinforcement strip 190 is coupled to a portion of the proximal region 130 of the aortic valve 120 and extends distally into the tapered region 150, positioned generally between the opposing flat surfaces 152 and 154 of the tapered region 150. In FIG. 18, a first elliptical reinforcement strip 191 is coupled entirely to the flat surface 152 of the tapered region 150, while a second longitudinal reinforcement strip 192 extends between the proximal region 130 and tapered region 150 and is positioned generally between the opposing flat surfaces 152 and 154 of the tapered region 150. In FIG. 19, a diamond-shaped reinforcement strip 193 is coupled between the proximal region 130 and the flat surface 152 of the tapered region 150. Like the reinforcement strips 185a-185c of FIGS. 14-16, the reinforcement strips 190-193 of FIGS. 17-19 may snap between two states during systole and diastole. In each of the embodiments of FIGS. 17-19, the reinforcement strips 190-193 advantageously provide a safety mechanism by which prolapse is avoided during retrograde flow. While various exemplary reinforcement strip shapes and locations are shown in FIGS. 14-19, the shapes and locations of the reinforcement strips may be varied, and greater or fewer strips may be used, without departing from the spirit of the present embodiments.

In still further embodiments, the stent structure 20 shown herein may be used in connection with different aortic valves, beside the aortic valve 120. Solely by way of example, and without limitation, various artificial valve designs may have two or three membranes, and may be arranged in various shapes including slots and flaps that mimic the natural functionality of an anatomical valve. Conversely, the aortic valve 120 shown herein may be used in conjunction with different stent structures.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A medical device for implantation in a patient, the medical device comprising:
   a stent having proximal and distal regions, and further comprising delivery and expanded states;
   a plurality of closed cells disposed at various locations between the proximal and distal regions of the stent; and
   a valve coupled to the stent,
   where the stent comprises at least four longitudinal regions in which a plurality of closed cells are disposed around a perimeter of the stent, where the first longitudinal region is disposed proximal to the second longitudinal region, the second longitudinal region is disposed proximal to the third longitudinal region, and the third longitudinal region is disposed proximal to the fourth longitudinal region,
   where an overall length of each of the closed cells of the first longitudinal region is less than an overall length of each of the closed cells of the second longitudinal region, and where the overall length of each of the closed cells of the second longitudinal region is less than an overall length of each of the closed cells of the third longitudinal region, and where the overall length of each of the closed cells of the third longitudinal region is less than an overall length of each of the closed cells of the fourth longitudinal region.

2. The medical device of claim 1, where each closed cell has an overall length, when the stent is in the expanded state, that is greater than a length of every other closed cell that is disposed proximally thereof.

3. The medical device of claim 1, where a plurality of closed cells disposed around a perimeter of the proximal region of the stent comprise a higher radial force relative to a plurality of closed cells disposed around a perimeter of the distal region of the stent.

4. The medical device of claim 1, where at least one of the closed cells comprises four angled strut segments, and where two of the angled strut segments comprise a greater length relative to the other two angled strut segments within the closed cell.

5. The medical device of claim 1, where at least one of the closed cells comprises four angled strut segments, and where two of the angled strut segments comprise a first width, which is greater than a second width of the other two angled strut segments within the closed cell.

6. The medical device of claim 1, where the proximal region of the stent comprises a cylindrical shape having a first outer diameter when the stent is in the expanded state, and where the distal region of the stent comprises a cylindrical shape having a second outer diameter when the stent is in the expanded state, where the second outer diameter is greater than the first outer diameter, the stent further comprising:
   a tapered region disposed between the proximal and distal regions, where the tapered region transitions the stent from the first outer diameter to the second outer diameter.

7. The medical device of claim 1, where the proximal region of the stent comprises a plurality of proximal apices, where at least one of the proximal apices has an end region having an integral barb formed therein, where the plurality of closed cells of the proximal region are disposed distal to the plurality of proximal apices.

8. A medical device for implantation in a patient, the medical device comprising:
   a stent comprising:
      a proximal region comprising a cylindrical shape having a first outer diameter when the stent is in an expanded state;
      a distal region comprising a cylindrical shape having a second outer diameter when the stent is in the expanded state, where the second outer diameter is greater than the first outer diameter;
      a tapered region disposed between the proximal and distal regions, where the tapered region transitions the stent from the first diameter to the second diameter;
   a valve coupled to at least a portion of the stent, the valve having proximal and distal regions;
   a plurality of closed cells disposed around the perimeter of the proximal region of the stent, and another plurality of closed cells disposed around the perimeter of the distal region of the stent,
   where the tapered region further comprises a plurality of closed cells disposed around the perimeter of the stent,
   where the stent comprises at least four longitudinal regions in which a plurality of closed cells are disposed around a perimeter of the stent, wherein the proximal region comprises two or more different longitudinal regions within its boundaries, and the tapered region and the distal region each comprise one or more longitudinal regions within their boundaries,
   where the two or more longitudinal regions within the boundaries of the proximal region comprise different axial lengths when the stent is in the expanded state.

9. The medical device of claim 8, where an overall length of each of the closed cells of the tapered region is greater than an overall length of each of the closed cells of the proximal region of the stent and less than an overall length of each of the closed cells of the distal region of the stent when the stent is in the expanded state.

10. The medical device of claim 8, where the proximal region of the valve is at least partially positioned within the proximal region of the stent, and where the distal region of the valve is at least partially positioned within one of the tapered and distal regions of the stent.

11. The medical device of claim 8, where the plurality of closed cells of the proximal region of the stent comprise a higher radial force relative to the plurality of closed cells of the distal region of the stent when the stent is in the expanded state.

12. The medical device of claim 8, where at least one of the closed cells of the distal region of the stent comprises four angled strut segments, and where two of the angled strut segments comprise a greater length relative to the other two angled strut segments within the closed cell.

13. The medical device of claim 8, where the proximal region of the stent comprises a plurality of proximal apices, where at least one of the proximal apices has an end region having an integral barb formed therein, where the plurality of closed cells of the proximal region are disposed distal to the plurality of proximal apices.

14. A medical device for implantation in a patient, the medical device comprising:
   a stent comprising:
      a proximal region comprising a cylindrical shape having a first outer diameter when the stent is in an expanded state;
      a distal region comprising a cylindrical shape having a second outer diameter when the stent is in the expanded state, where the second outer diameter is greater than the first outer diameter;

a tapered region disposed between the proximal and distal regions, where the tapered region transitions the stent from the first diameter to the second diameter;

a valve coupled to at least a portion of the stent, the valve having proximal and distal regions;

a plurality of closed cells disposed around the perimeter of the proximal region of the stent, and another plurality of closed cells disposed around the perimeter of the distal region of the stent, where the tapered region further comprises a plurality of closed cells disposed around the perimeter of the stent, where the stent comprises at least four longitudinal regions in which a plurality of closed cells are disposed around a perimeter of the stent, where a first longitudinal region, among the four longitudinal regions, comprises four strut segments bounding each of the plurality closed cells within the first longitudinal region, where first and second strut segments of each closed cell of the first longitudinal region comprise different lengths than third and fourth strut segments of each closed cell of the first longitudinal region, and where the lengths of the first and second strut segments of each closed cell of the first longitudinal region are between about 1.5 to about 4.0 times greater than lengths of the third and fourth strut segments of each closed cell of the first longitudinal region.

15. The medical device of claim 14, wherein the proximal region comprises two or more different longitudinal regions within its boundaries, and the tapered region and the distal region each comprise one or more longitudinal regions within their boundaries, where the two or more longitudinal regions within the boundaries of the proximal region comprise different axial lengths when the stent is in the expanded state.

16. The medical device of claim 14, where the proximal region of the valve is at least partially positioned within the proximal region of the stent, and where the distal region of the valve is at least partially positioned within one of the tapered and distal regions of the stent.

17. The medical device of claim 14, where the plurality of closed cells of the proximal region of the stent comprise a higher radial force relative to the plurality of closed cells of the distal region of the stent when the stent is in the expanded state.

18. The medical device of claim 14, where the proximal region of the stent comprises a plurality of proximal apices, where at least one of the proximal apices has an end region having an integral barb formed therein, where the plurality of closed cells of the proximal region are disposed distal to the plurality of proximal apices.

19. The medical device of claim 14, where each closed cell has an overall length, when the stent is in the expanded state, that is greater than a length of every other closed cell that is disposed proximally thereof.

* * * * *